United States Patent [19]

Slocum et al.

[11] Patent Number: 4,494,545
[45] Date of Patent: Jan. 22, 1985

[54] IMPLANT TELEMETRY SYSTEM

[75] Inventors: Chester D. Slocum; John R. Batty, Jr., both of Miami, Fla.

[73] Assignee: Cordis Corporation, Miami, Fla.

[21] Appl. No.: 406,367

[22] Filed: Aug. 9, 1982

Related U.S. Application Data

[62] Division of Ser. No. 153,093, May 27, 1980, Pat. No. 4,361,153.

[51] Int. Cl.$^3$ ............................................. A61N 1/36
[52] U.S. Cl. ................................ 128/419 P; 128/903
[58] Field of Search ............... 128/1.5, 653, 748, 903, 128/419 P, 419 PT

[56] References Cited

U.S. PATENT DOCUMENTS

| | | | |
|---|---|---|---|
| 3,371,272 | 2/1968 | Stanton | 128/1.5 |
| 4,063,551 | 12/1977 | Sweeney | 128/690 X |
| 4,163,447 | 8/1979 | Orr | 128/690 X |
| 4,270,545 | 6/1981 | Rodler | 128/653 |

Primary Examiner—Kyle L. Howell
Assistant Examiner—Francis J. Jaworski
Attorney, Agent, or Firm—Kenway & Jenney

[57] ABSTRACT

An externally generated myriametric frequency magnetic carrier signal is resonantly reflected by a tuned coil in an implant. The lagging phase angle of the reflected signal is modulated at very low power by varying the impedance across the tuned coil in accordance with a data input signal. An external phase shift demodulator recovers the transmitted data. To assure adequate coupling between the external unit and the implant, the output level of an external phase comparator must exceed a given threshold to signify "acquisition" before data is transmitted from the implant. In a preferred embodiment, a shunt circuit across the tuned coil is opened and closed in accordance with a digital input signal generated by the implant. The external telemetry unit preferably includes a coaxially spaced triple coil assembly. The middle coil transmits the carrier. The outer pickup coils are balanced to minimize carrier reception. For two-way communication an IR transmitter is added to the coil assembly. During acquisition, the output of the tuned coil is used to turn on a dormant IR receiver in the implant. Light emitting diodes are preferably mounted in an array on the face of the coil assembly surrounded by an optional reed switch coil for multimode telemetry in the programmer.

21 Claims, 21 Drawing Figures

IMPLANT TELEMETRY SYSTEM

This is a division, of application Ser. No. 153,093, filed May 27, 1980 now U.S. Pat. No. 4,361,153.

BACKGROUND OF THE INVENTION

The invention relates generally to wireless communication systems for isolated devices, and more particularly to electromagnetic signalling and telemetry systems for physiological implants and the like.

Externally applied oscillating magnetic fields have been used before with implanted devices. Early inductive cardiac pacers employed externally generated electromagnetic energy directly as a power source. A coil inside the implant operated as a secondary transformer winding and was interconnected with the stimulating electrodes. More recently, implanted stimulators with rechargeable (e.g., nickel cadmium) batteries have used magnetic transmission to coule energy into a secondary winding in the implant to energize a recharging circuit having suitable rectifier circuitry. Miniature reed switches have been utilized before for implant communications. They appear to have been first used to allow the patient to convert from standby or demand mode to fixed rate pacing with an external magnet. Later, with the advent of programmable stimulators, reed switches were rapidly cycled by magnetic pulse transmission to operate pulse parameter selection circuitry inside the implant. Systems analogous to conventional two-way radio frequency (RF) and optical communication systems have also been proposed.

The increasing versatility of implanted stimulators demands more complex programming capabilities. While various systems for transmitting data into the implant have been proposed, there is a parallel need to develop compatible telemetry systems for signalling out of the implant. However, the austere energy budget constraints imposed by long life, battery operated implants rule out conventional transmitters and analogous systems.

SUMMARY OF THE INVENTION

Accordingly, one of the chief goals of the present invention is to transmit an information signal from an implanted device while consuming the lowest possible amount of power. A related objective of the invention is to provide a compact implant telemetry system with practical physical requirements. Another related objective of this invention is to provide an implanted transmitter suitable for fast, accurate serial data transmission to interface with digital circuitry. A further objective is to provide an implant communication capability with excellent noise immunity and reliable low cost receiver circuitry.

These and other objects of the invention are achieved by the use of a resonant impedance modulated transponder in the implant to modulate the phase of a relatively high energy reflected magnetic carrier imposed from outside of the body.

The communications system according to the invention is specifically designed for transmitting information from a fixed internal implant (or other isolated device) to a positionable external telemetry unit. A relatively high energy magnetic field at a carrier frequency is established by a carrier transmitter in the external unit. The field permeates the skin, underlying tissue and case of the implant and induces a signal (voltage) in a resonant, impedance modulated transponder in the implant tuned to the carrier frequency. A secondary field is reradiated or reflected (used synonymously below) at the carrier frequency by the resonant transponder as well as by all other metallic features of the implant to varying degrees. The transponder feeds a load (terminating impedance) in the implant which may vary between the two extremes equivalent to an open circuit (infinite resistance) and a closed circuit (minimum resistance or shunt). Varying the impedance of the load into which the transponder is terminated in accordance with a modulation input signal causes a shift in the phase angle and amplitude of the transponder's contribution to the composite reflected signal which results in a proportional phase and amplitude shift in the composite reflected signal. The composite reflected signal is picked up, along with the attenuated carrier to some extent, and demodulated by a phase shift detector in the external telemetry unit. Thus the modulation input signal in the implant is transmitted out on the reflected signal and recovered in the external receiver. The implant, however, only consumes the energy necessary to modulated the transponders' load impedance. This energy level is very low compared to the energy of the total signal reflected by the transponder.

To assure adequate coupling between the external unit and the implant, the output level of an external phase comparator must exceed a given threshold to signify "acquisition" before data is transmitted from the implant. The comparator is responsive to the attenuated carrier and the received reflected signal whose amplitude varies with the spacing between the external unit and the implant. Thus, the combination of carrier and reflected signal has a phase angle which also depends on the position of the external unit.

In the preferred reflected signal telemetry system, a low resistance shunt circuit across an implanted coil capactively tuned to the carrier frequency is alternately opened and closed in accordance with a digital input signal, preferably a pulse width modulated binary signal, generated by the implant. The external telemetry unit includes a coaxially spaced triple coil assembly. The middle coil transmits the carrier. The differentially connected front and back pickup coils are balanced to lower the reception of the carrier so that the reflected signal, which is strongly picked up by the front coil, can be easily detected in the presence of the carrier.

In the preferred embodiment, the reflected signal telemetry system is coupled with an external infrared transmitter, to form a multimode two-way communications loop. The output of the tuned coil is used to activate a dormant optical receiver in the implant. In a hand-held multimode programmer/telemetry head, light emitting diode (LED's) are mounted in a coaxial array on the face of the triple coil assembly surrounded by an optional reed switch coil. The telemetry head transmits data to implants which have IR receivers or reed switch data receivers and receives data transmitted from the implant via the resonant transponder system.

For implants having paramagnetic metal cases of titanium or stainless steel, for example, the magnetic carrier signal is preferably in the myriametric frequency range from about 3 kilohertz (kHz) to about 30 kHz to which these metals are relatively transparent, more preferably in the upper audio band and optimally about 16 kHz.

In a specific embodiment of the implant telemetry receiver, the interval between zero crossings of the carrier and received reflected signal is timed by analog circuitry and converted to a dc phase angle voltage level. The phase detector output is subjected to signal processing circuitry which is immune to data inversion due to accidental misalignment of the external unit and the implant.

BRIEF DESCRIPTION OF THE DRAWINGS

Corresponding reference characters indicate corresponding parts throughout the several views of the drawings.

DESCRIPTION OF THE PREFERRED EMBODIMENT

Figure 1:
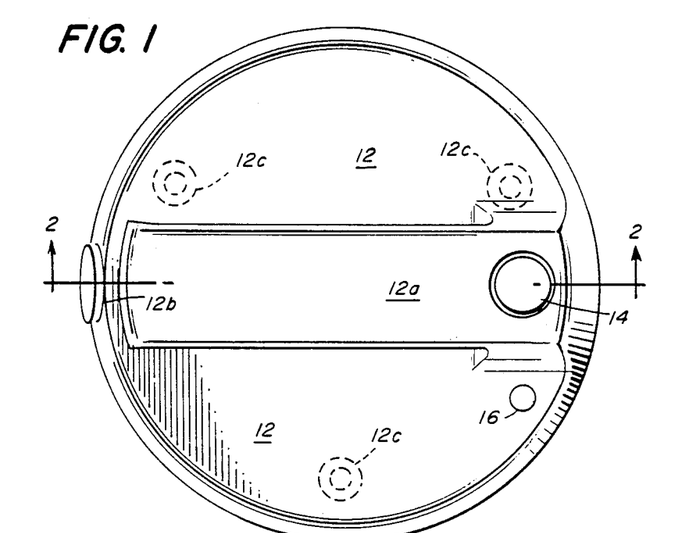
FIG. 1 is a plan view of a preferred embodiment of the telemetry head according to the invention.
Figure 2:
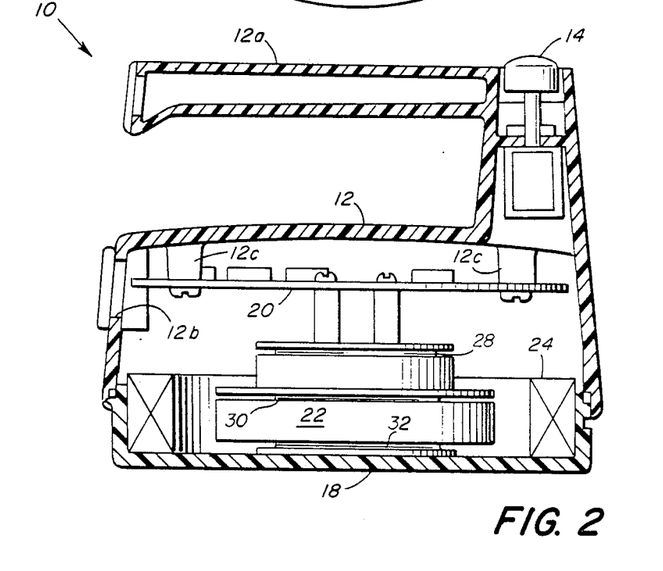
FIG. 2 is a cross-sectional view of the telemetry head taken along lines 2—2 of FIG. 1 with portions of the interior shown in elevation.

FIGS. 1 and 2 illustrate the physical aspects of a preferred hand-held two-way telemetry head 10 according to the invention. Telemetry head 10 includes an inverted cup-shaped upper shell 12 having an integral handle 12a with a pushbutton 14. The upper shell 12 is preferably a single injection molded part of acrylonitrile-butadiene-styrene (ABS) thermoplastic. The cup-shaped portion of the upper shell 12 includes a grommeted rear opening 12b for a cable (FIG. 9) and an indicator light 16 mounted on the upper surface thereof. A circular lower shell or lens 18 is designed to be snap-fit into the circular opening in the bottom of upper shell 12. The lens 18 is made of an injection molded thermoplastic which is relatively transparent to infrared wavelengths of light.

Inside the upper shell 12 a rigid disc-shaped printed circuit board 20 is suspended by a plurality of screws which engage downwardly projecting studs 12c, as shown in FIG. 2. The board 20 carries the various electrical components associated with the telemetry circuitry of FIGS. 10 and 13–16. A combined triple coil and LED assembly 22 is rigidly suspended from the printed circuit board 20 as shown in FIG. 2. The front face of the assembly 22 abuts the inside surface of the lens 18. An optional coil 24 (used to actuate reed switches for programming) surrounds the assembly 22 and is attached to the inside of the lens 18 for removal therewith.

Figure 3:
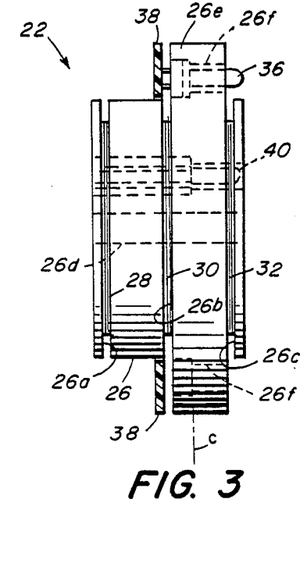
FIG. 3 is a side view of a combined triple coil and LED assembly inside the telemetry head of FIG. 1.
Figure 4:
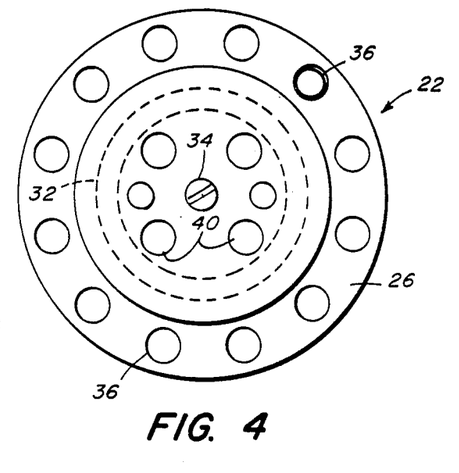
FIG. 4 is a front view of the face of the assembly of FIG. 3.

As shown in FIGS. 3 and 4 the coil and LED assembly 22 includes a plastic spool 26 with three similar coaxial annular grooves 26a, 26b and 26c, about 1 millimeter (mm) wide and 25 mm in inner diameter in which electrical coils 28, 30 and 32, respectively, are wound. The grooves are axially spaced so that the outer coils 28 and 32 are each displaced about 1 centimeter (cm) from the center coil 30. The axial distance between the front coil 32 and the adjacent face of the spool 26 should be as small as practical for example about 1 mm. A coaxial bore 26d in the spool 26 receives an axially adjustable brass tuning slug 34. On an integral coaxial annular flange 26e extending outwardly between the front coil 32 and middle coil 30, 12 IR LED's 36 are mounted in circumferentially equally spaced through holes 26f. The LED's may be secured by introducing a small amount of silastic or other potting material into the through holes. The beam leads on each LED 36 are plugged into an annular printed circuit board 38 arranged coaxially behind the flange 26e. Four more LED's 40 are symmetrically mounted inside of the front coil 32 in corresponding through-holes. The leads from the inner LED's 40 are electrically interconnected with board 38. All of the LED holes 26f are counterbored from the back to the reference plane c which is chosen such that the tips of the LED's 36 and 40 lie in the same plane as the front face of the spool 26.

Figure 5:
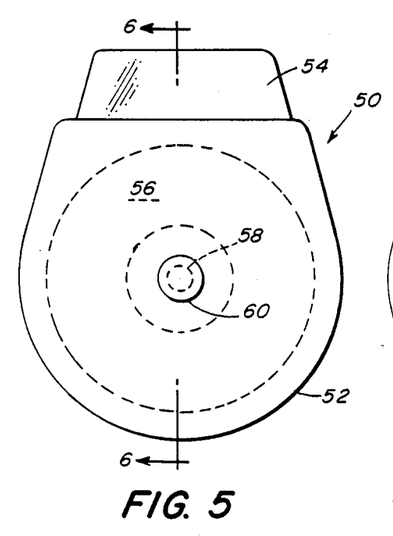
FIG. 5 is a plan view of an implant with a transponder coil in phantom.
Figure 6:
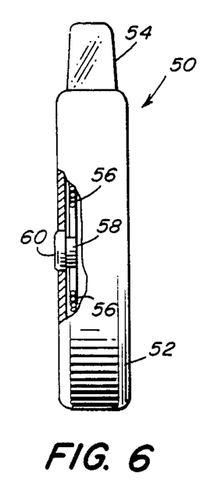
FIG. 6 is a side view of the implant of FIG. 5 with portions broken away to reveal the coil and photodiode.

FIGS. 5 and 6 illustrate an implantable physiological stimulator 50 or "implant", such as a neural stimulator or cardiac pacer of the type manufactured by Cordis Corporation, the assignee of the present application. The enclosure for the implant is hermetically sealed to avoid contaminating the electronic components. The enclosure typically comprises a relatively thin flat metal case 52, preferably a deep drawn container made of titanium, and a neck portion 54 of epoxy in which the electrical connectors for the stimulator leads are potted. A relatively large flat wound transponder coil 56 (FIG. 7) is mounted inside the metal case 52 parallel to the flat surface which lies closer to the patient's skin. The spacing between the coil and the inside of the case and other metallic components in the implant is preferably maximized to reduce stray capacitance which lowers the Q of the tuned coil as discussed below. The other components of the transponder are also located within the metal case 52 along with the internal components of the stimulator.

Figures 8, 9, 10, 11:
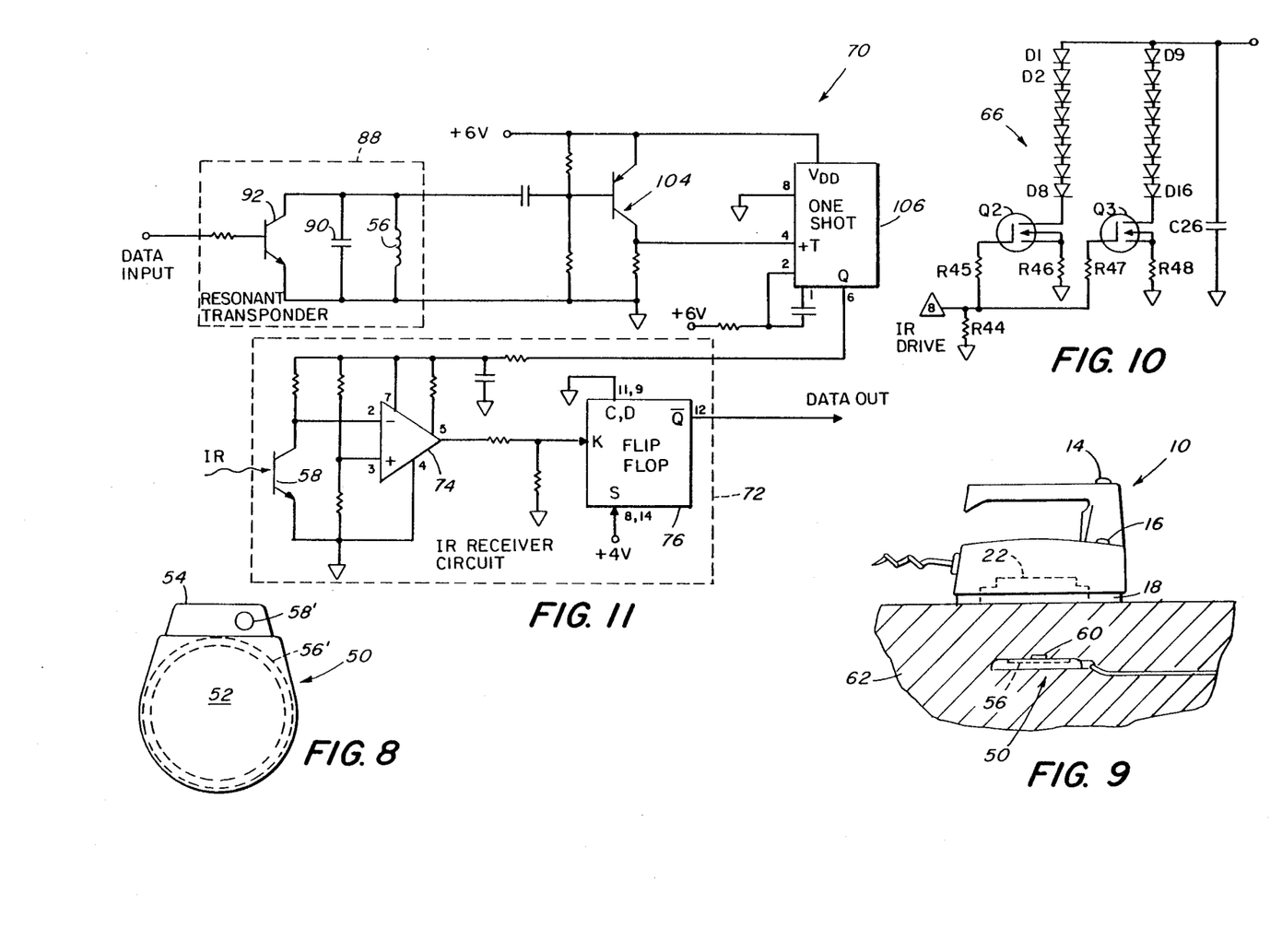
FIG. 8 is a plan view of an alternate embodiment of the implant of FIGS. 5 and 6.
FIG. 9 is a schematic representation of the use of the telemetry head of FIG. 1 with the implant of FIG. 5.
FIG. 10 is a schematic diagram of the optical transmitter circuit in the telemetry head of FIG. 1.
FIG. 11 is a schematic diagram of the optical receiver circuit and tuned coil transponder in a communications module for the implant of FIG. 5.

A semiconductor photodiode 58, or other photosensitive electrical element, is mounted in the implant 50 as shown in the alternate embodiments of FIG. 5 and FIG. 8. An infrared transparent window 60 preferably of sapphire is hermetically sealed in the center of the flat side of the titanium case 52 with the photodiode 58 located just beneath the window surrounded by the transponder coil 56, as shown in FIGS. 5 and 6.

Alternatively, the photodiode 58 is located in the IR transparent epoxy neck 54 as designated by reference numeral 58' in FIG. 8. Although the photodiode may be vulnerable to saline contamination in the permeable epoxy neck, this factor may turn out to be negligible over the life of the implant. FIG. 8 also illustrates in phantom an alternative ring configuration for the coil, designated coil 56'. A cylindrical coil with an axial thickness slightly less than the inside width of the case 52 is mounted inside the outer ring of the case. It is of course possible that the future may see the development of adequately nonpermeable plastic potting materials to replace the presently preferred metal case. This would ease the location requirements on both the photodiode and the coil.

FIG. 9 illustrates the physiological stimulator 50 of FIGS. 5 and 6 implanted with electrical leads connected in a suitable portion of a human body 62. The physician places the face of the telemetry head against the skin adjacent to the implant 50 for noninvasive two-way communication with the implant. A table-top programmer console (not shown) is connected by cable to the telemetry head.

Data Transmission to the Implant

The electronic circuitry associated with the IR data transmission into the implant is shown in detail in FIGS. 10 and 11. LED's 36 and 40 (FIG. 4) in the bottom of the telemetry head 10 correspond to the 16 diodes illustrated in the LED driver circuit 66 of FIG. 10. The circuit 66 is operated from the battery voltage supply, $V_{BB}$, for the telemetry head 10. Transistors Q2 and Q3 are N channel voltage operated metal oxide semiconductor (VMOS) field effect transistors (FET's) which drive the IR LED's D1-D16. IR LED's are preferred since they are more efficient at percutaneous transmission. A positive dc IR DRIVE signal (e.g., $V_{BB}$-2V) the input to line 8, lights the diodes simultaneously in a predetermined pulse width modulation code for data transmission from the telemetry head 10 to the implant.

FIG. 11 shows the implanted communications module 70 having an IR receiver circuit 72 which includes the photodiode 58 (FIG. 6) for receiving optically transmitted data from the telemetry head 10. The decrease in resistance of the photodiode 58 when exposed to infrared light lowers the voltage input to a linear amplifier 74 whose output resets a data flip-flop 76. The inverted output Q-bar of the flip-flop 76 provides the data output to decoder circuitry (not shown) in the implant. The data output is an exact replica of the data transmitted from the telemetry head.

In the preferred system, the pulse code for IR transmission is binary pulse width modulation: a 1 millisecond (ms) pulse is a binary "0", a 2 ms pulse is a binary "1", and the pulse-to-pulse period is 3 ms. A typical data word might comprise a string of 32 pulses.

Data Transmission from the Implant

Figure 12:
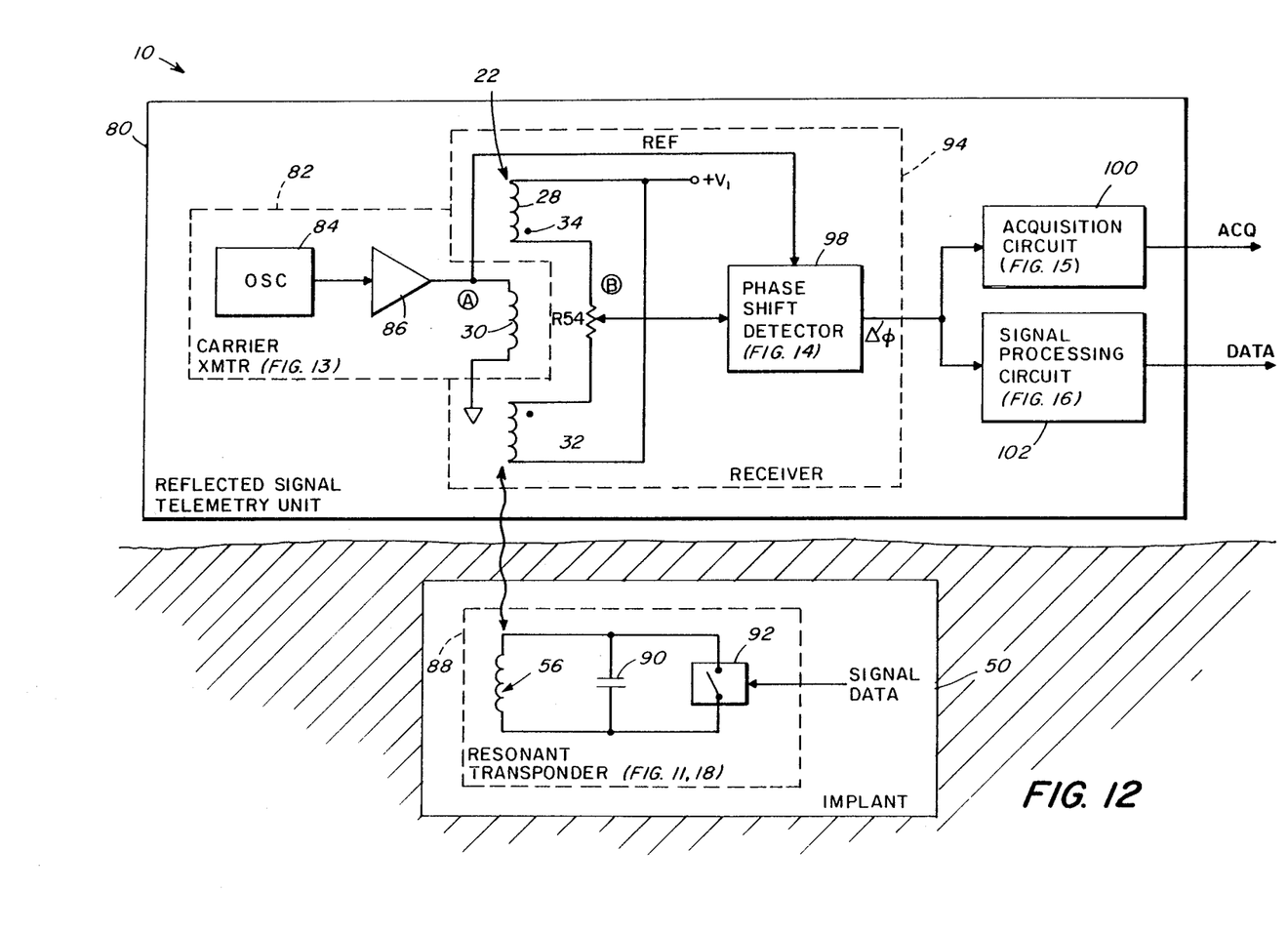
FIG. 12 is a block diagram of a preferred reflected signal telemetry system used by the telemetry head of FIG. 1 and implant of FIG. 5.

FIG. 12 provides an overview at the system level of the reflected signal telemetry system used for transmitting data from the implant. The external reflected signal telemetry unit 80 in the telemetry head 10 includes a carrier transmitter 82 having an oscillator 84 which produces a continuous wave myriametric frequency electrical output at about 16 kHz. The oscillator output is fed via a driver amplifier 86 to the middle coil 30 in the triple coil assembly 22.

Figure 7:
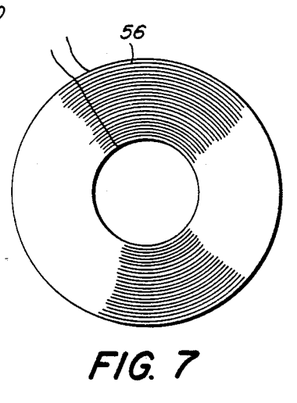
FIG. 7 is a detail plan view of the transponder coil in the implant of FIG. 5.

In the implant 50, the reflected signal transponder 88 includes the coil 56 (FIG. 7). The ends of the coil 56 are connected in parallel with a capacitor 90 and a semiconductor switch 92 which forms the load into which the tuned coil (i.e., coil 56 with capacitor 90) is terminated electrically. The resonant or bandpass frequency of the tuned coil is centered at the carrier frequency, 16 kHz. The oscillating current through the coil 30 in the telemetry head 10 establishes a magnetic field which radiates into the adjacent implant and induces a corresponding voltage in the tuned coil 56 which in turn reradiates a secondary magnetic field at the same carrier frequency. However, when conducting, the semiconductor switch 92 is a low resistance shunt across the tuned coil which removes the capacitive reactance of the transponder and thus slightly increases the amplitude and alters the phase of the reflected signal. The control input to the switch 92 is a digital data signal generated within the implant with the desired format of the pulse width modulation code (i.e., 1 ms and 2 ms switch closures with a pulse-to-pulse interval of 3 ms). A specific embodiment of the transponder 88 is shown in FIG. 11, in which the switch 92 is a bipolar NPN transistor. This arrangement facilitates referencing the output voltage across the coil 56 to negative ground, which is used, for example, is neural stimulators manufactured by Cordis Corp. Referencing the voltage to ground, however, is not essential to operation of the reflected signal telemetry system.

In the receiver 94 of the telemetry head 10 in FIG. 12, corresponding ends of the outer pickup coils 28 and 32 are interconnected by a potentiometer R54 and the other ends are connected to positive dc voltage ($+V_1$). A phase shift detector 98 is connected to point A in the output to the oscillator coil 30 in order to receive the carrier signal as a reference input. The wiper of potentiometer R54, picks off the differential voltage signal induced in the pickup coils 28 and 32 which forms input B to the phase shift detector 98. By comparing signal B with signal A, the phase shift detector 98 produces an output level indicative of the displacement of the phase angle of the received signal B relative to the carrier signal A. When the telemetry head 10 is in position for transmission (FIG. 9), signal B will include the reflected signal from the implanted transponder 88 as well as the attenuated carrier.

The phase angle output level of the detector 98 is passed to an acquisition circuit 100 which produces a logic output level indicative of acquisition when the output level of detector 98 exceeds a threshold value. During telemetry (i.e., data reception from the implant) the output of detector 98 is fed to a signal processing circuit 102 which reconstructs the data input signal modulating the phase angle of the received signal B.

The schematic diagrams in FIGS. 10 (IR XMTR) and 13-16 define specific telemetry head circuitry utilizing both discrete components and integrated circuits which, except for the coils and LED's, are located on the printed circuit board 20 (FIG. 2) in the telemetry head 10. The circuitry operates on three positive dc voltages $V_{BB}$, $V_1$ and $V_2$ (plus ground). $V_1$ and $V_2$ are derived from $V_{BB}$ by a voltage regulated power supply (not shown) in the telemetry head 10. Major input and output lines are indicated by upright triangles. These lines, along with $V_{BB}$ and ground, are connected by multiconductor cable to the aforementioned programmer console which produces the various enable signals and processes the acquisition and data outputs of the telemetry head 10. A table of exemplary values and designations of the components follows the discussion of FIG. 17.

Figures 13, 14:
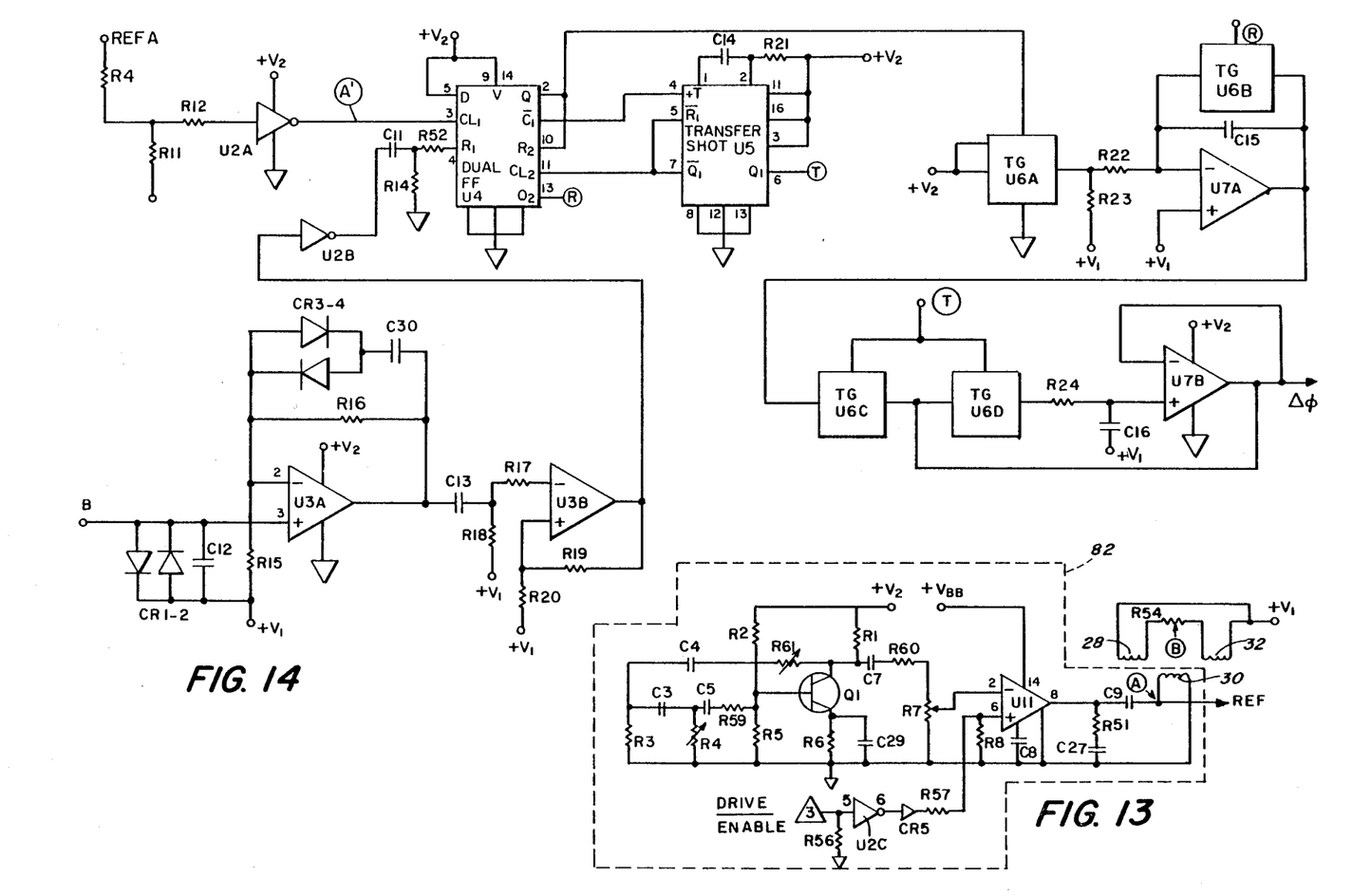
FIG. 13 is a schematic diagram of the carrier transmitter circuit in the reflected signal telemetry unit of FIG. 12.
FIG. 14 is a schematic diagram of the phase shift detector circuit in the reflected signal telemetry unit of FIG. 12.

FIG. 13 illustrates the carrier oscillator 84 followed by power amplifier 86, an integrated circuit U1, which drives the oscillator coil 30. The oscillator 84 is implemented by a phase shift oscillator with an output frequency tuned by resistor R4 to 16 kHz. Potentiometer R7 adjusts the output level of amplifier U1. The capacitor C9 and coil 30 form a series resonant circuit also tuned to 16 kHz. A high frequency suppression network is provided by resistor R51 and capacitor C27.

Muting of the transmitter 82 is accomplished by pulling DRIVE ENABLE line number 3 low. When DRIVE ENABLE is high, the transmitter is on. Diode CR5 provides noise immunity at amplifier U1 since pin 6 of U1 is an analog input with a gain of 50.

The front coil 32 is the primary reflected signal receiving coil. The back coil 28 is used to balance out the transmitted signal. This balancing is accomplished by manipulating the potentiometer R54 and the slug 34 in the coil assembly 22 (FIG. 4). Complete nulling of transmitted signal reception is probably neither feasible nor desirable.

The phase shift detector 98, shown in FIG. 14, is a zero crossing phase comparator. An integrator produces a dc voltage proportional to the difference in phase between the transmitted signal A and the received signal B.

Signal A is attenuated by resistive network R9 and R11 and squared up by a Schmidt trigger U2A. (A letter following an integrated circuit designation such as U2 specifies an identical integrated circuit or fraction of a multiple circuit.) Signal B from the pickup coils (pot. R54, FIGS. 12, 13) is amplified and limited by operational amplifier U3A then squared up by U3B and U2B. Diodes CR1 and CR2 limit the input swing into U3A, for example, to 1 volt peak-to-peak. The capacitor C30 assures symmetrical limiting regardless of the offset voltage out of amplifier U3A.

The squared up reference signal A sets the integrate latch U4 (first flip-flop in dual flip-flop U4) whose output Q1 (line I) turns on the analog integrator U7A. The squared up received signal B resets the integrate latch which stops the integration. When the integrate latch line I goes low, a transfer one-shot U5 produces a pulse T for about 1 microsecond to operate the gates U6C and U6D. The voltage across integrating capacitor C15 is then transferred through transmission gates U6C and U6D to the sample and hold amplifier U7B. When the output pulse T goes low, the second flip-flop circuit in U4 is set. The Q2 output of the second flip-flop retsets the integrator through the R output line to clear the integrator for the next cycle.

Resistor R23 (FIG. 14) following transmission gate U6A provides a pull down to the same potential as the noninverting input of the integrator U7A to insure that integration is completely stopped. Resistor R25, and the transmission gates U6C and U6D form a low leakage sample and hold gate by feeding back the hold voltage from U7B to reduce the potential difference across U6D to near zero. The output of sample and hold circuit U7B, which forms the output of detector 98, is a dc voltage representing the phase shift or phase angle between the reference carrier signal A and the received signal B from the pickup coils 28 and 32. The system is preferably calibrated so that the output of U7B is about 20 millivolts per degree phase shift at 16 kHz. An increase in the phase lag, for example by shunting the tuned coil in the transponder 88 (FIG. 12) normally results in a lower output level from the phase detector 98.

Figures 15, 16:
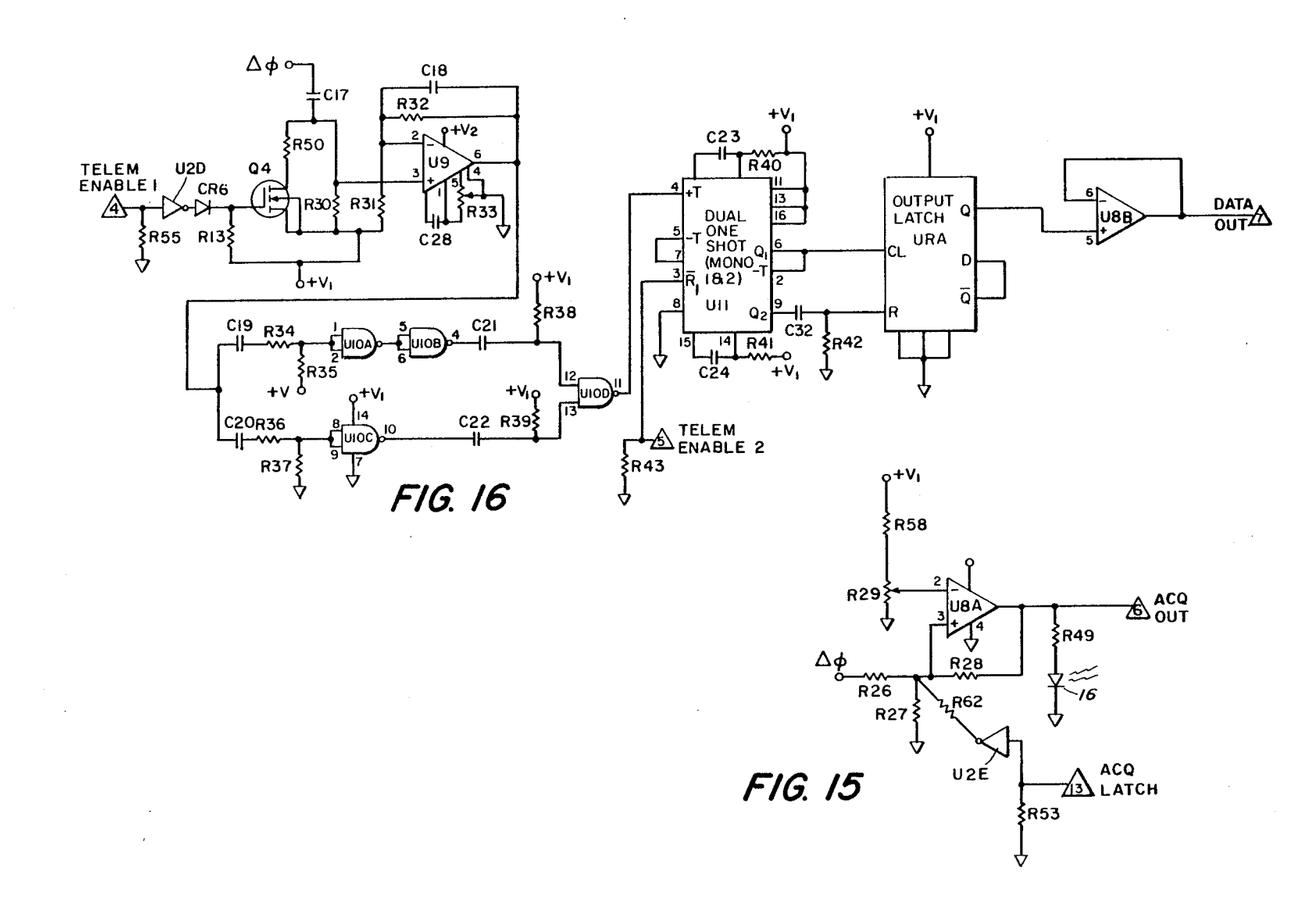
FIG. 15 is a schematic diagram of the acquisition circuit in the reflected signal telemetry unit of FIG. 12.
FIG. 16 is a schematic diagram of the signal processing circuit in the reflected signal telemetry unit of FIG. 12.

FIG. 15 illustrates an acquisition circuit 100 which senses the proximity of the telemetry head 10 to the implant 50 (FIGS. 9 and 12). The dc phase angle voltage is applied to the non-inverting input of a comparator U8A with an adjustable threshold. As the telemetry head 10 moves closer to the optimum position, the relative phase signal declines. In a device constructed in accordance with the invention, the phase has been observed to decline from above 200° to a minimum of about 100° when approaching the implant. With 20 millivolt per degree sensitivity, the comparator U8A threshold is adjusted to 4 volts. When the phase shift goes below about 200°, the comparator output (U8A, pin 1) goes high, the LED D17 glows (for indicator light 16 of FIG. 1) and the acquisition output line 6 goes high. If desired, instead of using a comparator, the dc phase angle voltage could be converted to an analog signal to drive a meter calibrated to indicate acquisition.

The phenomenon observed in the changing phase of signal B (prior to modulation of the resonant transponder 88) with varying spacing of the telemetry head 10 from the implant 50 suggests that the reflected signal is changing in phase. However, this is probably not the predominant factor as the impedance of the implant remains unchanged. What appears to be a more important contributor is that the pickup coils 28 and 32 mix or sum the fixed amplitude attenuated carrier with the received reflected signal which has an amplitude which varies with distance. Since the received reflected signal is lagging in phase (whether or not the phase angle is fixed), the combination (B) of the carrier and reflected signal exhibits changing phase as the weight of the quadrature component changes. Fortunately, for this reason it appears to be preferable not to completely remove the carrier from the pickup coils.

Once acquisition has been obtained, it is desirable to keep the acquisition LED D17 glowing during a subsequent two-way data transmission. This is accomplished by Schmidt trigger U2E forcing the input to U8A high. Input line 13 to U2E is normally high, when looking for acquisition of the implant. Line 13 goes low to latch the acquisition light on during subsequent telemetry action.

In FIG. 12, each time the switch 92 closes, an artifact is produced in the composite reflected signal from the implant, namely a discrete phase shift. The relative phase of the received signal B has been observed to change, for example, from 151 degrees to 195 degrees, when the tuned coil is shunted out. Both the amplitude change and the phase change of the actual reflected signal are believed to contribute to the phase shift appearing in signal B. The ac portion of the signal at the output of the phase shift detector 98 (FIGS. 12 and 14) thus represents phase modulation by the implanted transponder 88.

Figure 17:
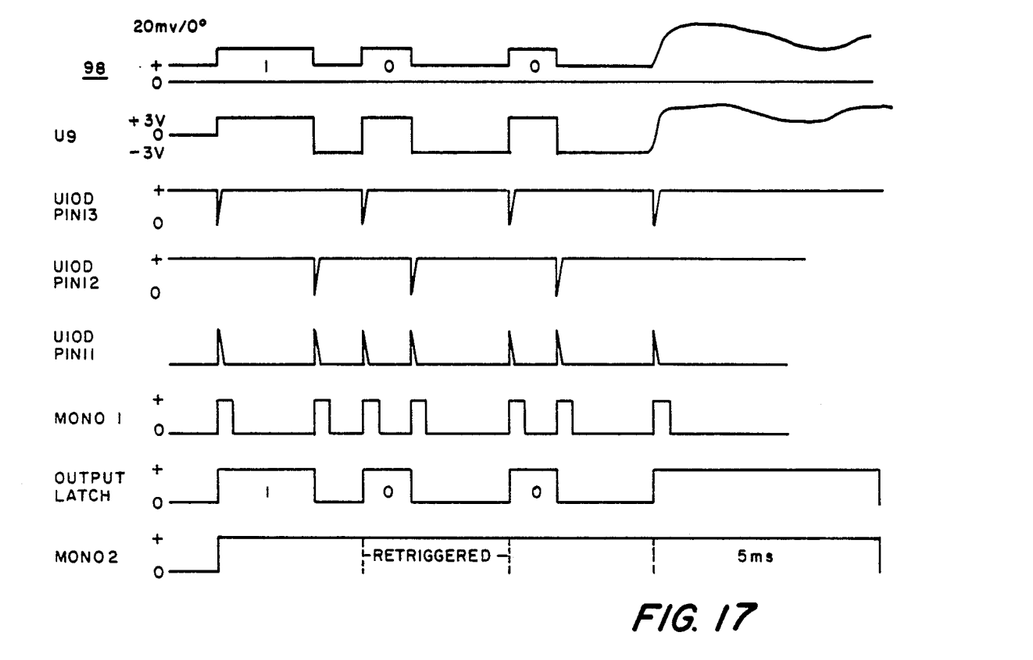
FIG. 17 is a timing diagram for signals associated with the circuit of FIG. 16.

Although the phase modulation could be analog, binary pulse width modulation is preferred as shown in the top line of FIG. 17 illustrating the phase angle voltage waveform from detector 98. By design, a pulse (switch closure) of 1 ms duration is designated as a binary "0", a 2 ms duration represents a binary "1", and the pulse-to-pulse repetition period is 3 ms, long enough for about 48 cycles of the carrier frequency. This code format is identical to that used for IR transmission into the implant.

FIG. 16 illustrates the signal processing circuit 102 which performs the final demodulation and reproduces the transmitted data from the dc phase angle voltage. When the linear amplifier U9 is enabled by the TELEMETRY ENABLE 1 (signal on line 4) going low, the dc phase angle voltage is boosted to logic levels. The amplified signal operates the dual channel Schmidt trigger arrangement U10A–U10C to trigger the first one-shot in dual one-shot circuit U11. This combination of logic circuitry adds to the noise immunity of the system. The output of the first one-shot (mono No. 1) of U11 is used to trigger both the output latch U12 and the second one-shot (mono No. 2) of U11. Mono No. 2 is a missing pulse detector which resets the output latch after 5 ms of inactivity. The output of latch U12 is buffered by voltage follower amplifier U88 whose output forms the data output of the telemetry lead 10 with positive logic TTL level pulse width modulated code.

The purpose of the TELEMETRY ENABLE 1 signal (line 4) in FIG. 16 is to hasten the settling time of the linear amplifier U9 after a transient caused for example by turning on the power amplifier (DRIVE ENABLE) or infrared or reed switch programming transmission from the telemetry head. The circuit comprised of transistor Q4, resistors R50 and R13 and diode CR6 represents a time constant shortening circuit. Resistor R50 has much lower resistance than R30. Thus by pulling down line 4 (e.g. to 0 volts), Q4 is turned on and the normal time constant (C17×R30) is reduced to (C17×R50), 0.15 ms instead of 1.5 ms, for example. Thus, a step response at the output of the sample and hold circuit U7D will clear at the input to linear amplifier U9 in less than 1 ms. It is desirable to shorten the time constant whenever telemetry is not being received from the implant. TELEMETRY ENABLE 2 goes high (e.g., +6 volts) to enable mono No. 1 of U11 and low to blank unwanted data by holding mono No. 1 off whenever telemetry is not being received.

As indicated in the timing diagram of FIG. 17, the NAND gate U10D inputs (FIG. 16) are normally high. One channel is responsive to the rising edge of the transition in the phase angle voltage when the transponder is keyed, and the other channel is responsive to the falling edge. As the direction of transition can reverse itself under certain conditions of misalignment of the lead and implant, this dual channel system provides immunity to data inversion. In each channel the respective transition is differentiated to briefly pulse the respective trigger input to the NAND gate low. The output of the NAND gate U10D is a full string of upright pulses corresponding to transitions in the phase angle voltage. These pulses operate mono No. 1 (U11) which has a brief (e.g., 100 microsec.) on time. The rising edge of mono No. 1 toggles the output latch to reproduce the transmitted data. Mono No. 2 is also triggered by the rising edge of mono No. 1 and resets the output latch after 5 ms of inactivity without being retriggered. This function prevents the output latch from being left in the high state indefinitely by noise, as illustrated in FIG. 17.

The following table provides representative values and designations for the components of the circuits of FIGS. 10 and 13–16. These specific components merely serve as an example of one specific embodiment of circuitry for carrying out the invention in a specific application. Other embodiments may of course have substantially different components, yet still be within the scope of the invention.

TABLE

| | | | | | |
|---|---|---|---|---|---|
| R1 | 10 | kilohms | C3 | 560 | picofarads |
| R2 | 68 | " | C4 | " | " |
| R3 | 8.2 | " | C5 | " | " |
| R4 | 20 | " | C7 | 630 | picofarads |
| R5 | 10 | " | C8 | 0.68 | microfarad |
| R6 | 3.3 | " | C9 | 0.22 | " |
| R7 | 5 | " | C10 | 0.01 | " |
| R8 | 1 | kilohm | C11 | 560 | picofarads |
| R9 | 10 | kilohms | C12 | 0.001 | microfarad |
| R11 | 6.8 | " | C13 | 0.01 | " |
| R12 | 2 | " | C14 | 100 | picofarads |
| R13 | 10 | " | C15 | 0.001 | microfarad |
| R14 | 5.1 | " | C16 | 0.002 | " |
| R15 | 5.1 | " | C17 | 1.5 | microfarads |
| R16 | 1 | megohm | C18 | 120 | picofarads |
| R17 | 1 | kilohm | C19 | 0.01 | microfarad |
| R18 | 1 | " | C20 | 0.01 | " |
| R19 | 100 | kilohms | C21 | 220 | picofarads |
| R20 | 1 | kilohm | C22 | " | " |
| R21 | 10 | kilohms | C23 | 150 | " |
| R22 | 51 | " | C24 | 0.01 | microfarad |
| R23 | 1 | kilohm | C26 | 100 | microfarads |
| R24 | 1 | " | C27 | 0.1 | microfarad |
| R25 | 100 | kilohms | C28 | 50 | picofarads |
| R26 | 15 | " | C29 | 0.1 | microfarad |
| R27 | 1 | kilohm | C30 | 0.01 | " |
| R28 | 1 | megohm | C32 | 680 | picofarads |
| R29 | 1 | kilohm | Q1 | 2N930 | |
| R30 | 1 | kilohm | U1 | LM380 | |
| R31 | 1 | " | U2 | CD40106BE | |
| R32 | 300 | kilohms | U3 | CD3240DE | |
| R33 | 100 | " | U4 | CD4013BE | |
| R34 | 2 | " | U5 | CD4098BE | |
| R35 | 100 | " | U6 | CD4016BE | |
| R36 | 2 | " | U7 | CA3240AE | |
| R37 | 100 | " | U8 | CA3240AE | |
| R38 | 51 | " | U9 | CA3130S | |
| R39 | 5 | " | U10 | CD4093BE | |
| R40 | 620 | " | U11 | CD4098BE | |
| R41 | 1 | megohm | U12 | CD4013BE | |
| R42 | 51 | kilohms | one-shot | 106 CD4098 | |
| R43 | 1 | kilohm | flip-flop | 76 CD4013 | |
| R44 | 10 | kilohms | amplifier | 74 LM3078 | |
| R45 | 1 | kilohm | | | |
| R46 | 1 | " | | | |
| R47 | 10 | ohms | | | |
| R48 | 10 | " | | | |
| R49 | 120 | " | | | |
| R50 | 100 | " | | | |
| R51 | 2.7 | ohms | | | |
| R52 | 2 | kilohms | | | |
| R53 | 2 | " | | | |
| R54 | 20 | " | | | |
| R55 | 2 | " | | | |
| R56 | 2 | " | | | |
| R57 | 10 | " | | | |
| R58 | 15 | " | | | |
| R59 | 68 | " | | | |
| R60 | 43 | " | | | |
| R61 | 50 | " | | | |
| R62 | 10 | " | | | |
| D1–D16 | 920 nanometer wavelength, 0.4 amp. | | | | |
| Coil 30 | 300 turns (25 mm dia.) No. 34 gauge enameled copper wire | | | | |
| Coils 28, 32 | 100 turns (25 mm dia.) No. 40 gauge enameled copper wire | | | | |
| Coil 56 | 100 flat wound turns of No. 34 gauge enameled copper wire with 4 cm outer diameter and 2 cm inner diameter | | | | |
| Coil 24 | 84 turns of 14 gauge enameled copper wire | | | | |

TABLE-continued

|  | driven at 20 amps. |
|---|---|
| $V_{BB}$ | +17.5 volts |
| $V_1$ | +6 volts |
| $V_2$ | +12 volts |

Operation

The operational sequence for two-way communication between the telemetry head 10 and the implant 50 involves three distinct phases: an acquisition mode, a transmission or programming mode in which data is sent to the implant, followed by a reflected signal telemetry mode in which data is sent from the implant to the telemetry head. There are two modalities for data transmission to the implant, namely, IR transmission and conventional magnetic pulse transmission. Both may use the same pulse width modulated code format. In the preferred system, however, the implant is equipped with an IR receiver.

The following sequence of actions illustrates a typical two-way communication initiated by a physician who desires to program new stimulation pulse parameters for an implant. The physician decides on and selects the desired parameters at the programming console and then turns on the electrical power ($V_{BB}$) to the telemetry head. The telemetry carrier transmitter 82 is activated by DRIVE ENABLE going high. The physician positions the telemetry head 10 over the implant 50 as shown in FIG. 9. When the threshold phase shift is detected by acquisition circuit 100, the indicator light 16 (diode D17) is turned on. In the meantime, inside the implant, with reference to FIG. 11, the voltage induced in the passive transponder coil 56 is applied by a transistor switch 104, which turns on at 0.6 volts, for example, to trigger one-shot 106 which activates the formerly dormant IR receiver circuit 72. If the implant has a reed switch data receiving circuit in lieu of an IR receiver, this activating step is unnecessary. The IR transmission mode begins when the physician presses the pushbutton 14 (FIG. 1) which applies $V_1$ to an output line connected to the programmer console. If magnetic pulse transmission were being used instead of IR transmission the DRIVE ENABLE signal would go low to turn off the carrier transmitter during magnetic pulse transmission to avoid interference. However, if IR transmission is used, the carrier transmitter may remain on. IR DRIVE signals are produced from the console in accordance with the preselected pulse parameters chosen by the physician. The string of IR pulses representing the first data word, for example, is transmitted and received and decoded in the implant.

In the reflected signal telemetry mode, acquisition is first reverified by turning on the carrier transmitter 82 if it has been turned off in the meantime and relighting the indicator light 16 on the telemetry head. Next with reference to FIG. 16 the TELEMETRY ENABLE 1 signal goes high and 1 ms later the TELEMETRY ENABLE 2 signal goes high. Data transmitted by the transponder 88 can now be received and processed by the telemetry lead 10. After reflected signal telemetry from the implant, TELEMETRY ENABLE 2 goes low and TELEMETRY ENABLE 1 goes low. At this point IR transmission can be resumed. In this manner the implant can answer back to confirm the programming data after each data word or string of programming pulses. After the last string of pulses has been sent and verified by telemetry the electrical power to the programming head is turned off which deactivates the acquisition indicator 16.

Figure 18:
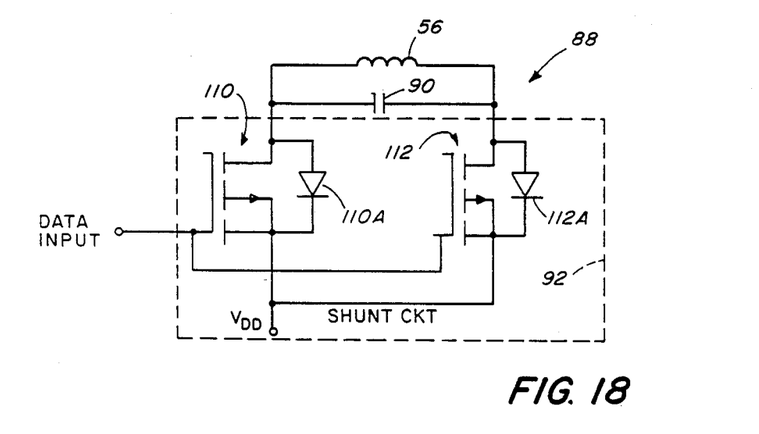
FIG. 18 is a schematic diagram of an alternate embodiment of the tuned coil transponder circuit.

FIG. 18 illustrates an alternate embodiment of the resonant transponder 88 in which the switch 92 for shunting the tuned coil 56 and capacitor 90 is implemented by a pair of P channel VMOS FET's 110 and 112. Each of these transistors has a built-in parasitic diode 110a, 112a from source to drain which lowers the on resistance during the inverted operation, that is to say, when the drain is more positive than the source. The diodes as well as the transistors are connected in series opposition so that one of the diodes is always reverse-biased. The complementary symmetry removes any tendency for the shunt circuit to exhibit different characteristics on the positive and negative half cycles of the signal across the tuned coil. Current flowing in the shunt circuit passes primarily through FET 110 and diode 112a on one half cycle and through FET 112 and diode 110a on the other half cycle. The common input signal to the gates of the transistors 110 and 112 is toggled between on and off voltage levels in accordance with the coded data input signal. In a cardiac pacer of the type manufactured by Cordis Corp., positive ground is used and each transistor is turned on by applying about −4 volts to the gate with respect to the source.

Figure 19:
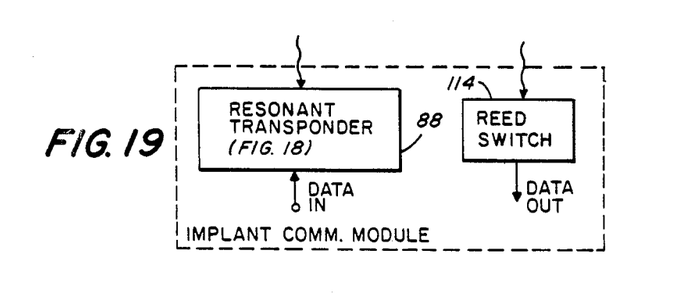
FIG. 19 is a block diagram of an implant communications module with a reed switch for receiving externally transmitted data.

The arrangement of FIG. 18 is suitable for cardiac pacers and other stimulators which employ a reed switch 114, as shown in FIG. 19, in lieu of an IR receiver for receiving programming pulses. In such systems the transmission to the implant phase is carred out by pulsing the large reed switch coil 24 (FIG. 2) in the telemetry head 10 according to a similar pulse width modulated code or a length-coded string of identical pulses, for example. During magnetic pulse transmission, the carrier transmitter 82 in the head is turned off to avoid adversely affecting the operation of the reed switch. Afterwards, the transmitter 82 is turned back on to enable reflected signal telemetry from the transponder 88 of FIG. 18. Thus the reed switch coil 24 and IR transmitter 66 (FIG. 10) in the telemetry head 10 represent alternative modes of data transmission into the implant. However, even implants which have IR receivers might include a reed switch which can be operated by the patient with a magnet for turning the implanted stimulator on or off in an emergency. The reed switch coil 24 could, of course, be used for this purpose as well if desired.

Figure 20:
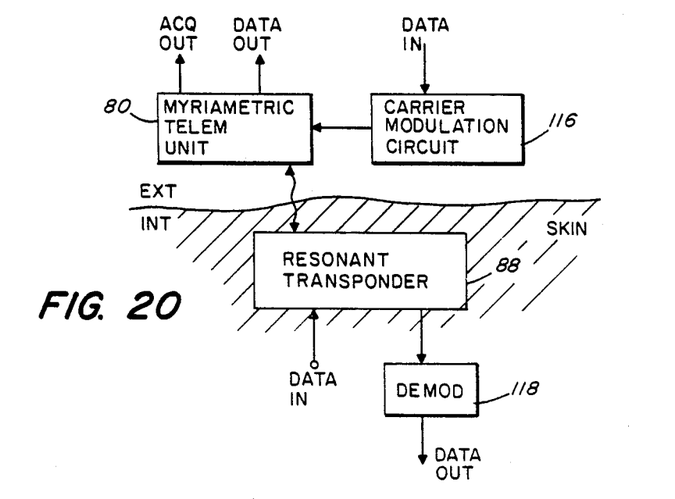
FIG. 20 is a block diagram of a communication system in which the transponder doubles as a receiver for carrier modulated transmission.
Figure 21:
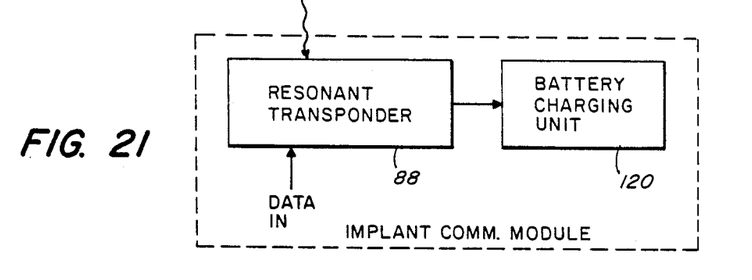
FIG. 21 is a block diagram of a communications module for an implant with a battery charger energized by the output of the transponder.

The tuned coil in the transponder 88 lends itself to other uses illustrated in FIGS. 20 and 21. FIG. 20 shows an alternative means of data transmission into the implant. The carrier generated by the carrier transmitter 82 in the reflected signal telemetry unit 80 of the head 10 is modulated by a carrier modulation circuit 116 which superimposes a data signal on the radiated magnetic carrier. The modulated carrier is picked up by the tuned coil in the transponder 88, acting as a secondary winding, and fed to a demodulator circuit 118 to recover the transmitted information signal. Thus the transponder 88 in this case doubles as a data receiver and data transmitter. However, IR transmission is preferred because of its immunity to common electromagnetic interference.

In FIG. 21 the tuned coil in the transponder 88 is also used as the secondary in a transformer type battery charger 120 including suitable rectifier circuitry. AC voltage induced in the coil of the transponder 88 by an externally generated field, which would be at an energy level higher than that produced by the myriametric carrier transmitter 82, is rectified and used to charge the batteries (e.g., nickel cadmium) supplying power to the implant.

A variety of modulation systems and carrier frequencies can be used in accordance with the invention. Selection of the myriametric frequency range (3 kHz to 30 kHz) coincides with the low pass 30 kHz cutoff characteristic of titanium and stainless steel leak proof implant cases. The optimum frequency selection depends on several factors. First, the Q of the implanted tuned coil is impaired by the capacitance created by the nearby case and other metallic components. The Q tends also to further decrease with increasing frequency. Thus 25 kHz, while within the low pass window, results in greater losses. Below 10 kHz the number of cycles per 3 ms pulse-to-pulse interval is low enough to introduce decoding errors. Moreover, it takes more energy at lower frequencies to induce the same voltage. Increasing the pulse-to-pulse interval lengthens data transmission times. The upper audio band (optimally 16 kHz) represents a happy medium between these extremes. This is somewhat surprising because it is well within the audio frequency band for loud speakers, for example, and because of the ubiquitous neighboring 15 kHz noise of the sync signal television frequencies. However, these noise factors do not present an interference problem since the sync signal is mostly electrostatic instead of magnetic and both audio and sync signals are rejected by the phase demodulation circuitry. Thus any frequency in the vicinity of 16 kHz is ideal. In other environments, however, with other modulation schemes, a different frequency may prove to be optimum for the telemetry system of the invention.

Any type of input signal code modulation can be used for reflected signal telemetering. The result will be corresponding phase modulation of the received signal. The controlled impedance across the transponder 88 may be a continuously variable resistance for example varying in accordance with an analog input signal. Digital code is preferred for medical applications because of its noise rejection capability and compatibility with the type of data to be transmitted, namely, pulse parameter selection codes.

The telemetry systems disclosed herein can be used separately or in various combinations. Two different modes can be used simultaneously, if desired, to transmit identical code for greater noise immunity. These systems may also be suitable for other low energy, telemetry applications for isolated devices.

The analog timing circuitry for the phase detector 98 and signal processing circuit 102 can be implemented as desired by digital timing circuitry. However, the disclosed analog system can resolve one degree of phase at 16 kHz, and a one degree phase interval represents a scant 174 nanoseconds. To count at twice that rate would require clock frequencies in excess of 10 megahertz.

Reflected signal telemetry uses the lowest possible current drain because practically all of the power comes from outside of the implant. The compact physical dimensions of the resonant transponder disclosed herein are compatible with space constraints within an implant. Phase modulation is detectable in a single cycle (or half cycle), has inherently low interference and accomodates digital pulse transmission techniques. The same pulse width modulation code can be used for reflected signal telemetry from the implant and for IR or magnetic pulse transmission to the implant. IR transmission provides fast digital data with low interference, and when used in conjunction with the reflected signal telemetry system, the implanted transponder can turn on a dormant IR receiver to conserve power and to provide a dual mode access code for data reception. The transponder coil thus has numerous functions including telemetry, activation of the IR receiver, and enhancement of the acquisition mode and is further adaptable for modulated carrier reception and battery charging functions. Physically and electrically, the triple coil assembly is compatible with a compact array of IR LED's which forms a relatively low cost, light weight compact two-way telemetry head.

As various changes could be made in the above constructions without departing from the scope of the invention, it should be understood that all matter contained in the above description or shown in the accompanying drawings shall be interpreted as illustrative and not in a limiting sense.

What is claimed is:

1. External data telemetry apparatus for receiving data communications from a biomedical implant, comprising
   a coil assembly having at least three coaxial spaced electrical coils,
   transmitter means operatively interconnected with a middle one of said coils for radiating a magnetic carrier signal,
   means for providing a pickup signal indicative of the difference between the voltages induced in at least one pair of other ones of said coils on opposite sides of said middle coil,
   phase shift detector means operatively connected to receive said pickup signal for producing an output signal level as a function of the relative phase angle of said pickup signal,
   and information signal processing means for digitally demodulating said output signal level to recover a digitally encoded data signal from said implant,
   whereby digitally modulated resonance within the implant is effectively employed as a low power communications medium.

2. The apparatus of claim 1, further comprising means for level detecting the output of said phase detector means for producing an acquisition signal.

3. The unit of claim 1, wherein the frequency of said carrier signal is in the audio band.

4. The apparatus of claim 1, wherein the frequency of said carrier signal is in the upper audio band.

5. The apparatus of claim 4, wherein the frequency of said carrier signal is approximately 16 kHz.

6. The apparatus of claim 1, further comprising means for electrically balancing the coupling of the carrier frequency into said other two coils including an axially adjustable brass slug mounted within said coil assembly.

7. The apparatus of claim 6, wherein said balancing means further includes a potentiometer interconnecting corresponding ends of said other coils, the wiper of said potentiometer providing said pickup signal.

8. The apparatus of claim 1, further comprising infrared light emitting means mounted on said coil assembly, and driver circuit means for modulating said light emitting means in accordance with an information signal,
   whereby data can be transmitted to the implant to provide two-way communication capability.

9. The apparatus of claim 1, further comprising a plurality of light emitting electrical elements mounted on said coil assembly in a coaxial array approximately coplanar with a front one of said other coils, and driver circuit means for simultaneously pulsing said elements on and off in accordance with an information signal.

10. The apparatus of claim 9, wherein a portion of said plurality of elements in said array is located inside of said front coil.

11. The apparatus of claim 1, wherein said coils are relatively spaced in the axial dimension.

12. The apparatus of claim 11, wherein said coils are approximately the same diameter.

13. The apparatus of claim 11, wherein said coils are equally spaced in the axial dimension.

14. The apparatus of claim 11, wherein said coil assembly includes an electrically insulating spool, said coils being coaxially mounted on said spool.

15. The apparatus of claim 14, further comprising an electrically insulating housing having a generally cylindrical portion coaxially containing said spool, said housing further including means defining a handle.

16. The apparatus of claim 15, further comprising an electromagnet coil disposed in said cylindrical portion of said housing coaxially with said spool, said electromagnet coil having a larger diameter than the coils on said spool, and transmitter means for pulsing said coil in accordance with a data signal, whereby electromagnetic impulses conveying information are transmitted to the implant to provide two-way communications capability.

17. The apparatus of claim 1, wherein said signal processing means includes pulse width demodulating means.

18. The apparatus of claim 1, wherein said signal processing means includes missing pulse detecting means.

19. External data telemetry apparatus for inbound telemetry to a biomedical implant, comprising a movable handheld telemetry head with a substantially flat bottom surface, a plurality of light emitting elements arranged in said head adjacent to said flat surface in a circular array about a common axis, and drive means for pulsing said elements simultaneously in accordance with a variable information carrying data signal.

20. The apparatus of claim 19, further comprising another plurality of light emitting elements being arranged in another circular array with a smaller radius coaxially and coplanarly mounted on said head within said one circular array, means for interconnecting said pluralities of elements for simultaneous actuation.

21. External data telemetry apparatus for receiving data communications from a biomedical implant, comprising a triple coil assembly having three coaxial spaced electrical coils, transmitter means operatively interconnected with the middle one of said coils for radiating a magnetic carrier signal, the other coils having corresponding ends electrically connected together in a series circuit, a pickup lead having one end connected to a junction between corresponding ends of said other coils, the other end of said pickup means providing a pickup signal indicative of the difference between the voltages induced in said other coils, information signal processing means connected to receive said pickup signal for demodulating the relative phase angle of said pickup signal to recover a transmitted data signal from said implant, whereby modulated resonance within the implant is effectively employed as a low power communications medium.

* * * * *